US005638810A

United States Patent [19]
Yavitz

[11] Patent Number: 5,638,810
[45] Date of Patent: Jun. 17, 1997

[54] INTRAORAL DEVICE

[76] Inventor: Edward O. Yavitz, 3828 Spring Creek Rd., Rockford, Ill. 61114

[21] Appl. No.: 341,361

[22] Filed: Nov. 17, 1994

Related U.S. Application Data

[63] Continuation-in-part of Ser. No. 254,990, Jun. 7, 1994, Pat. No. 5,462,049.

[51] Int. Cl.⁶ .................... A62B 7/10; A62B 23/02; A61C 3/00
[52] U.S. Cl. .................. 128/205.27; 128/205.29; 128/207.14; 128/836; 433/215; 433/229
[58] Field of Search ............ 128/203.15, 203.12, 128/205.27, 205.29, 207.14, 836; 433/215, 229

[56] References Cited

U.S. PATENT DOCUMENTS

| | | |
|---|---|---|
| 704,017 | 7/1902 | Fowler . |
| 712,304 | 10/1902 | Jacobs et al. . |
| 893,213 | 7/1908 | Whiteway . |
| 3,774,601 | 11/1973 | Langone . |
| 3,795,744 | 3/1974 | Ogawa et al. . |
| 4,071,026 | 1/1978 | Bevins . |
| 4,326,525 | 4/1982 | Swanson et al. .......... 424/19 |
| 4,388,328 | 6/1983 | Glass . |
| 4,485,118 | 11/1984 | Carroll et al. . |
| 5,052,410 | 10/1991 | Stubbs . |
| 5,167,964 | 12/1992 | Muhammad et al. .......... 424/482 |

*Primary Examiner*—Kimberly L. Asher
*Attorney, Agent, or Firm*—Robert A. Van Someren

[57] ABSTRACT

The present invention is directed to an intraoral device that can be used for absorbing tar and nicotine or dispensing various substances over a period of time. The device includes a flexible pad which is disposed within the mouth of a wearer. A plurality of tar and nicotine absorbent particles are embedded in the flexible pad. Often, a retainer portion is attached to the flexible pad to engage the teeth of the wearer for holding the flexible pad in a desired position within the wearer's mouth. Additionally, the flexible pad may also be impregnated with a breath freshener or medications having enteric coatings.

15 Claims, 2 Drawing Sheets

INTRAORAL DEVICE

This is a continuation-in-part of patent application Ser. No. 08/254,990, filed Jul. 7, 1994, now U.S. Pat. No. 5,462,044 and entitled "Intraoral Smoke Removal Device."

FIELD OF THE INVENTION

The present invention relates generally to a device for supplying medication orally, and particularly to an intraoral device designed for placement in the mouth of an individual to supply medication orally at a controlled rate. According to another aspect of the present invention, the intraoral device includes encapsulated medication that is released into the mouth of the wearer at a controlled rate.

BACKGROUND OF THE INVENTION

Various devices for removing contaminants from the air prior to inhalation are currently known. For example, a variety of masks are available which can be placed over the nose and mouth of the wearer to filter various airborne contaminants. Additionally, many brands of cigarettes already include self-contained filters which remove a portion of the tar and nicotine as it is inhaled through the cigarette.

Other devices have been designed for intraoral use. Filter devices have been designed for insertion between the teeth and lips of a wearer to filter the air inhaled by the wearer. Such devices generally include a screen or filter material.

Although some of these devices may work well, they are awkward and impractical to use on a day-to-day basis. For example, if a smoker wishes to remove a greater amount of the tar and nicotine from the smoke inhaled, it would be inconvenient to wear a mask or filter device covering the entire opening of the smoker's mouth. Additionally, such conventional filter devices are readily seen and unsightly in appearance.

Another disadvantage of existing devices is their failure to remove or cover the bad odors of many contaminants, such as the tar or nicotine in cigarette smoke. It would be beneficial to have an intraoral device convenient to use and not visible to common observers, yet able to remove at least a portion of the airborne contaminants.

Other than contaminant removal, intraoral devices could potentially be used for introducing substances into the mouth of the wearer. For example, the intraoral device could be used to dispense mouth freshener or medication into the mouth of the wearer. However, existing devices do not provide for introduction of substances into the wearer's mouth. There are time-release capsules that release medication over a sustained period of time, but those capsules must be ingested by the user.

The present invention addresses the drawbacks of current personal intraoral devices.

SUMMARY OF THE INVENTION

The present invention features an intraoral device for absorbing airborne contaminants, such as tar and nicotine normally inhaled or ingested by a smoker. The intraoral device comprises a generally flexible pad configured for insertion into the mouth of a wearer. The pad is configured to lie longitudinally within the mouth of the wearer to absorb airborne contaminants without obstructing the intake of substance through the wearer's mouth.

According to another aspect of the invention, the intraoral device is specifically designed to absorb tar and nicotine. In this embodiment, a flexible pad is configured to lie along the palate of a wearer. A plurality of tar and nicotine absorbent particles are embedded into the flexible pad. Additionally, a retainer portion is attached to the flexible pad to engage a tooth of the wearer to secure the flexible pad in proximity to the wearer's palate.

According to another aspect of the invention, a method is presented for removal of contaminants from air prior to the air entering that individual's lungs. The method includes the steps of forming a flexible pad configured for insertion into a wearer's mouth and embedding contaminant absorbent material into the flexible pad.

According to another aspect of the invention, an intraoral device is designed for freshening the breath of a user over a sustained period of time. The intraoral device includes a chewable pad. The device also includes a first flavored bit having an enteric coating of a first general thickness and a second flavored bit having an enteric coating of a second general thickness.

According to a further aspect of the invention, the intraoral device is designed to release medication over a sustained period of time. The pad includes a predetermined amount of one or more medicinal substances that may be divided into portions and coated with enteric coatings. Preferably, at least some of the portions have enteric coatings of different thicknesses so the medication may be released into the wearer's mouth at a controlled rate.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENT

Figure 1:
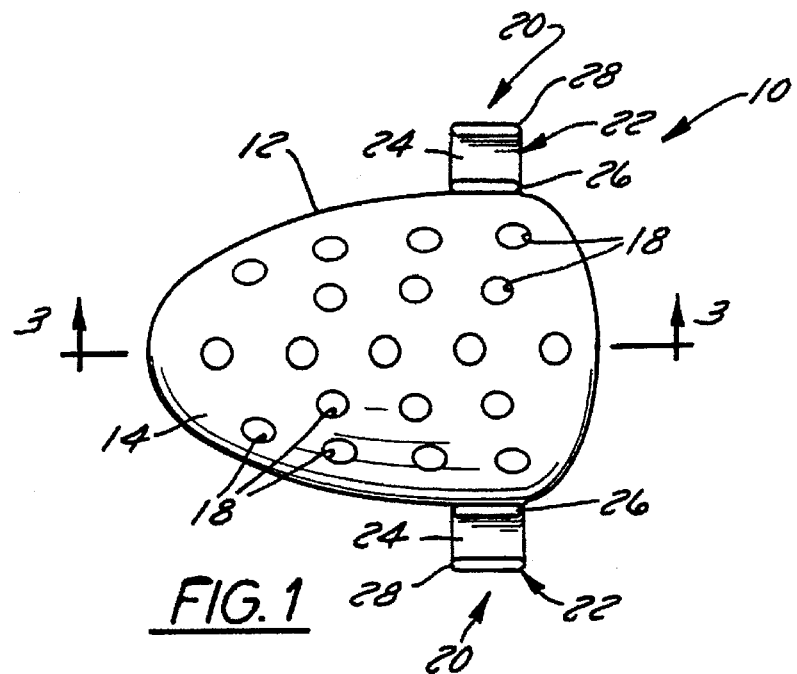
FIG. 1 is a top plan view of an intraoral device according to a preferred form of the present invention.
Figure 2:
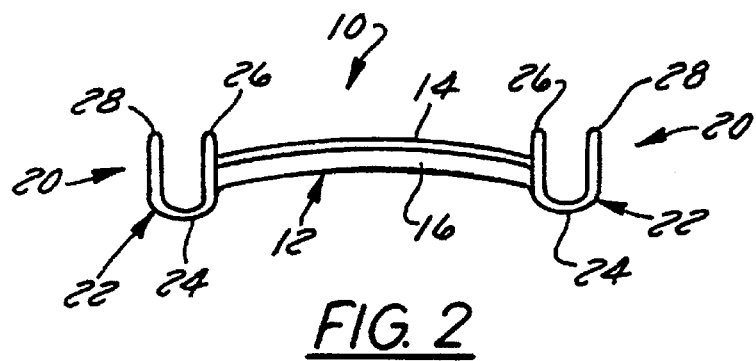
FIG. 2 is a front elevation view of the device shown in FIG. 1.
Figure 3:
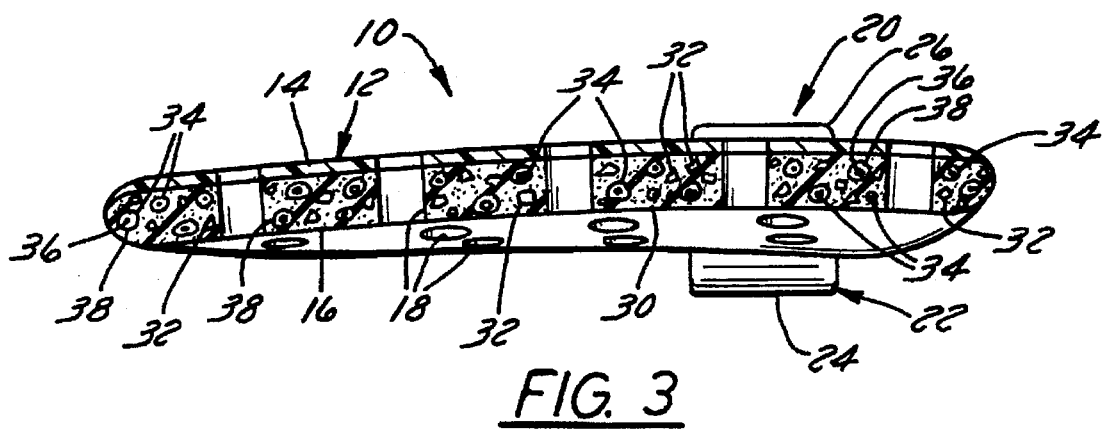
FIG. 3 is a cross sectional view taken generally along line 3—3 of FIG. 1.

A preferred embodiment of an intraoral device 10, according to the present invention, is illustrated in FIGS. 1—3. Intraoral device 10 is designed to fit within the mouth of a wearer and to supply remove noxious airborne contaminants, such as tar and nicotine. The device may be particularly helpful to smokers who wish to cut down on the amount of tar and nicotine which would otherwise be inhaled into his or her lungs.

Referring generally to FIG. 1, intraoral device 10 includes a flexible pad 12 configured for insertion into the mouth of a wearer. Flexible pad 12 may be designed for insertion into a variety of locations within the wearer's mouth, including disposition between the teeth and cheeks i.e. the buccal vestibule area of the human mouth. However, the pad is preferably configured to lie generally longitudinally along the roof of the mouth. Thus, as smoke or other contaminants are breathed into the mouth, flexible pad 12 is positioned to absorb at least some of the passing airborne contaminants.

Pad 12 preferably includes an upper layer 14 (see FIG. 2) which engages or lies along the palate of the wearer. Upper layer 14 is generally a non-absorbing material, such as a non absorbing plastic, to prevent prolonged contact between the contaminants absorbed by flexible pad 12 and the surface of the wearer's mouth. Pad 12 also includes a lower layer 16 which preferably lies adjacent upper layer 14 and is attached to upper layer 14. Lower layer 16 is the layer exposed to the airborne contaminants to absorb at least certain of the airborne contaminants.

A plurality of fenestrations 18 extend through flexible pad 12 in a generally transverse direction to layers 14 and 16 and allow air flow therethrough. Fenestrations 18 may be pores or openings as shown in FIG. 1 and are designed to allow air flow therethrough in case intraoral device 10 becomes dislodged and positioned in the throat of the wearer.

Optionally, intraoral device 10 includes a retainer portion 20 attached to flexible pad 12. Retainer portion 20 may have various configurations to hold flexible pad 12 between the wearer's teeth, along side the wearer's teeth, or over the wearer's teeth. In the illustrated embodiment, retainer portion 20 includes two extensions 22 designed to fit over the wearer's molar teeth and to hold pad 12 along the wearer's palate. Each extension 22 includes a base 24, an inner tab 26, and an outer tab 28. Inner tab 26 and outer tab 28 cooperate to grip a tooth or a plurality of teeth of the wearer. This securely holds device 10 in the desired location while remaining virtually unnoticeable to other persons interacting with the wearer.

As illustrated generally in FIG. 3, flexible pad 12 is designed to absorb airborne contaminants, e.g. tar and nicotine. In a preferred embodiment, lower layer 16 is a foam rubber layer 30 impregnated with a contaminant absorbent material 32, such as activated charcoal particles. The foam rubber material 30 is sufficiently porus to allow absorption of contaminants by the activated charcoal throughout lower layer 16.

Flexible pad 12 may also be at least partially impregnated with a breath freshening substance 34. Breath freshening substance 34 can include liquid, crystals, or vapors contained within the foam rubber material 30. In the illustrated embodiment, the breath freshening substance 34 is in the form of flavor crystals having flavored bits 36 encapsulated by enteric coatings 38. Some of the breath freshening crystals omit enteric coating 38 to provide instantaneous freshening once intraoral device 10 is placed in the wearer's mouth. Other flavor crystals 36 are encapsulated by enteric coatings 38 are be dissolved by the saliva of the wearer to provide a later release of breath freshener. By encapsulating flavor crystals 36 with enteric coatings of different thicknesses, the release of breath freshener is maintained over a longer period of time.

For example, a first group of flavored crystals 36 may have relatively thin enteric coatings. A second group of the flavored crystals may have enteric coatings which are somewhat thicker than those of the first group. A third group of flavored crystals may be coated with a still thicker enteric coating to provide multiple groups of flavor crystals to release flavor and/or breath freshener at different times. Generally, when the flavor crystals are used up, the tar and nicotine absorbing particles 32 of pad 12 will be at least partially saturated and the device can then be disposed of.

Figure 4:
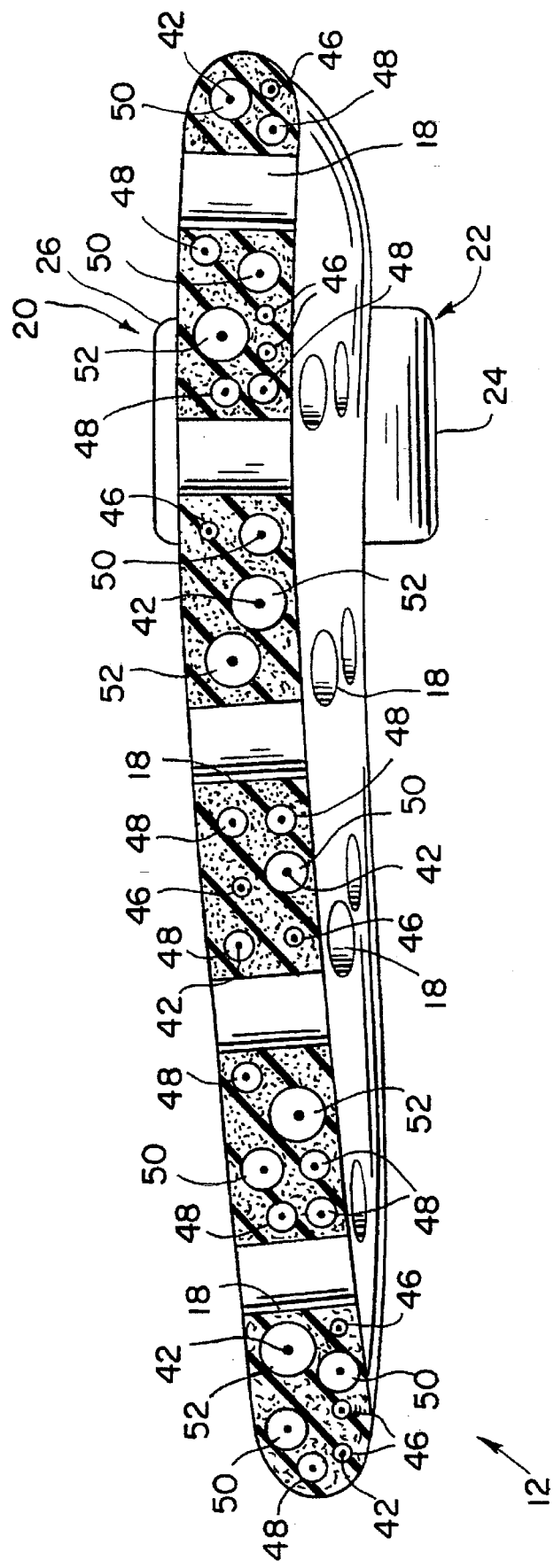
FIG. 4 is a cross sectional view of an alternate embodiment of the intraoral device having medication releasing capsules.

Flexible pad 12 may also be at least partially impregnated with a medicinal substance 40 in place of or in combination with breath freshening substance 34 and absorbent material 32. (See FIG. 4.) In this embodiment, it may not be necessary to include upper layer 14. Also, for some applications, the flexible pad should be configured to fit between the wearer's teeth and cheek. However, it may still be advantageous to clip flexible pad 12 to at least one of the wearer's teeth via retainer portion 20.

In this embodiment, flexible pad 12 includes a predetermined dosage of one or more medicinal substances 40. Preferably, the medicinal substance or substances 40 are divided into a plurality of portions or particles 42 that are distributed throughout at least part of flexible pad 12. Particles 42 dissolve within the mouth of the wearer to provide medication to the wearer over a sustained period of time. The length of this period can be controlled by placement of the particles or by creating particles of different sizes; however, it is preferred that the particles or portions 42 are coated with enteric coatings 44 that are dissolved by saliva within the wearer's mouth to release the medicine therein. By coating different particles with enteric coatings of different thicknesses, the rate of release of the medication can be controlled over a substantial period of time.

For example, some of the portions or particles 42 may be covered with a relatively thin enteric coating 46. Other portions 42 may be covered with a slightly thicker enteric coating 48. Still other portions 42 may be covered with an enteric coating 50 having a third thickness that differs from the enteric coatings 46 and 48. Still other portions 42 may have enteric coatings 52 that are quite thick to provide for a substantial delay prior to the release of medication from the encapsulated portions 42. The portions 42 can also be covered with a much greater range of enteric coatings with different thicknesses, depending on the type of medication, the need for consistency of release, and the length of time over which it is to be released.

A variety of medications can be administered to the individual wearing flexible pad 12, and the following list should not be considered inclusive. However, examples of medications that can be administered via flexible pad 12 include viscous xylocaine, antiseptic agents, flouride, continuous antiacid, various antibiotics, nitroglycerin and acetazolamide.

It will be understood that the foregoing description is of preferred exemplary embodiments of this invention and that the invention is not limited to the specific forms shown. For example, intraoral device 10 may have a variety of configurations to accommodate insertion into various regions of the wearer's mouth. A variety of plastic, rubber, or other materials acceptable for intraoral placement may be used to construct the intraoral device. Similarly, a variety of contaminant absorbent materials, breath freshening substances or medications can be interchanged. These and other modifications may be made in the design and arrangement of the elements without departing from the scope of the invention as expressed in the appended claims.

What is claimed is:

1. An intraoral device for providing medication to a user, comprising:
   a pad conformed to fit the palate of a human mouth, the pad including:
   an airborne contaminant absorber;
   a first surface configured to lie along the palate of a human mouth; and
   an exterior absorbent surface exposed to the tongue of a human mouth;
   a predetermined dosage of medication embedded in the pad, wherein the predetermined dosage of medication comprises a plurality of particles distributed through at least a portion of the pad; and
   wherein at least some of the particles have enteric coatings exposed to the tongue of the wearer.

2. The intraoral device of claim 1, further comprising a retainer portion attached to the flexible pad, the retainer portion engaging a tooth of the wearer to secure the flexible pad within the mouth of the wearer.

3. The intraoral device of claim 1, wherein the thickness of the enteric coatings varies between particles.

4. The intraoral device of claim 3, wherein the pad includes pores which allow the passage of air therethrough.

5. A method for providing medication orally to an individual over a controlled period of time, the method comprising the steps of:

forming a flexible pad configured for insertion into a wearer's mouth;

embedding the flexible pad with a medicinal substance;

providing the medicinal substance with an enteric coating; and attaching a retainer to the flexible pad to grip at least one tooth of the wearer and to secure the flexible pad within the wearer's mouth.

6. The method for providing medication as recited in claim 5, further comprising the step of impregnating the flexible pad with a flavored substance.

7. The method for providing medication as recited in claim 5, further comprising the step of impregnating the flexible pad with a plurality of breath freshening flavor crystals having enteric coatings.

8. The method of providing medication as recited in claim 5, further comprising the steps of dividing the medicinal substances into portions and encapsulating the portions with enteric coatings of differing thicknesses.

9. The method for providing medication as recited in claim 8, further comprising the step of connecting a retainer to the flexible pad to facilitate retention of the flexible pad along the palate of the individual.

10. An intraoral device for providing medication orally to an individual over a sustained period of time, comprising:

a pad conformed to fit the buccal vestibule of a human mouth, the pad including:

a first surface configured to lie along an interior surface of a human mouth; and an exterior absorbent surface exposed to the tongue of a human mouth;

a retainer portion attached to the pad, the retainer portion being configured to grip at least one tooth of a wearer to secure the pad within the human mouth;

a first portion of a medicinal substance having a first enteric coating of a first general thickness; and a second portion of a medicinal substance having a second enteric coating of a second general thickness, wherein the first portion and the second portion are embedded in the pad and further wherein the first enteric coating and the second enteric coating are exposed to the tongue of the individual.

11. The intraoral device as recited in claim 10, further comprising a third portion of the medicinal substance having a third enteric coating of a third general thickness.

12. The intraoral device as recited in claim 11, further comprising a fourth portion of the medicinal substance having a fourth enteric coating of a fourth general thickness.

13. The intraoral device as recited in claim 12, wherein there are a plurality of first portions, a plurality of second portions, a plurality of third portions, and a plurality of fourth portions.

14. The intraoral device as recited in claim 11, wherein there are a plurality of first portions, a plurality of second portions, and a plurality of third portions.

15. The intraoral device as recited in claim 10, wherein there are a plurality of first portions and a plurality of second portions.

* * * * *